US010930902B2

(12) United States Patent
Wu

(10) Patent No.: US 10,930,902 B2
(45) Date of Patent: Feb. 23, 2021

(54) LOCKABLE FITTING STRUCTURE FOR AN ELECTRIC AIR-PURIFYING RESPIRATOR OF AN AUTO-DARKENING WELDING HELMET

(71) Applicant: Tecmen Electronics Co., Ltd., Nanjing (CN)

(72) Inventor: Ziqian Wu, Nanjing (CN)

(73) Assignee: Tecmen Electronics Co., Ltd., Nanjing (CN)

( * ) Notice: Subject to any disclaimer, the term of this patent is extended or adjusted under 35 U.S.C. 154(b) by 1041 days.

(21) Appl. No.: 15/329,004

(22) PCT Filed: Sep. 1, 2015

(86) PCT No.: PCT/CN2015/088743
§ 371 (c)(1),
(2) Date: Jan. 25, 2017

(87) PCT Pub. No.: WO2016/169181
PCT Pub. Date: Oct. 27, 2016

(65) Prior Publication Data
US 2018/0337373 A1    Nov. 22, 2018

(30) Foreign Application Priority Data

Apr. 22, 2015 (CN) .......................... 2015 1 0194247

(51) Int. Cl.
*H01M 2/10* (2006.01)
*A62B 9/00* (2006.01)
(Continued)

(52) U.S. Cl.
CPC ............. *H01M 2/1022* (2013.01); *A61F 9/06* (2013.01); *A61F 9/068* (2013.01); *A62B 7/10* (2013.01);
(Continued)

(58) Field of Classification Search
CPC ..... A62B 18/00; A62B 18/003; A62B 18/006; A62B 7/10; A62B 9/00; A62B 9/04;
(Continued)

(56) References Cited

U.S. PATENT DOCUMENTS 5,151,727 A * 9/1992 Sasaki .................. H04N 5/2256
348/730
8,257,851 B2    9/2012 Tang
(Continued)

FOREIGN PATENT DOCUMENTS

CN        101222030 A     7/2008
CN        101771139 A     7/2010
(Continued)

OTHER PUBLICATIONS

Machine translation of WO-2014119192-A1 (Year: 2014).*
(Continued)

*Primary Examiner* — Joseph D. Boecker

(57) ABSTRACT

The present application discloses a lockable fitting structure used for an electric air-purifying respirator of an auto-darkening welding helmet, the electric air-purifying respirator comprising a housing and a battery device, a battery holder being formed in the housing, and the battery device being able to be detachably installed in the battery holder by the lockable fitting structure, wherein the lockable fitting structure comprises at lease four pairs of sliding joint structures formed on the battery device and the battery holder respectively and a locking structure provided in the battery device, wherein the sliding joint structures of each pair can be engaged with or disengaged from each other by sliding them relative to each other, wherein the locking structure comprises a button and a tongue capable to be actuated by the button, wherein the tongue is movable along a direction substantially perpendicular to a sliding direction of the sliding joint structure, and wherein after the sliding
(Continued)

joint structures have been moved relative to each other in place, the tongue contacts a stop side of the battery holder to lock the pairs of sliding joint structures. The present application also discloses an electric air-purifying respirator for an auto-darkening welding helmet, which is equipped with said lockable fitting structure.

20 Claims, 7 Drawing Sheets

(51) Int. Cl.
*A61F 9/06* (2006.01)
*A62B 7/10* (2006.01)
*A62B 9/04* (2006.01)

(52) U.S. Cl.
CPC .................. *A62B 9/00* (2013.01); *A62B 9/04* (2013.01); *H01M 2/10* (2013.01); *H01M 2/1055* (2013.01); *H01M 2/1066* (2013.01); *H01M 2220/30* (2013.01)

(58) Field of Classification Search
CPC ... A61F 9/06; A61F 9/068; A42B 3/28; A42B 3/286; A42B 3/288; H01M 2/1022; H01M 2/1033; H01M 2/1055; H01M 2/1066; H01M 2220/30
See application file for complete search history.

(56) References Cited

U.S. PATENT DOCUMENTS

| | | | |
|---|---|---|---|
| 9,331,317 B2 | 5/2016 | Takeshita et al. | |
| 2002/0034683 A1* | 3/2002 | Takeshita ................ | H01M 2/30 429/123 |
| 2005/0200330 A1 | 9/2005 | Ahn et al. | |
| 2006/0285330 A1 | 12/2006 | Sundell | |
| 2007/0240716 A1* | 10/2007 | Marx ................... | A62B 18/006 128/204.21 |
| 2007/0270194 A1* | 11/2007 | Park .................... | H04M 1/0262 455/575.1 |
| 2009/0055987 A1 | 3/2009 | Becker et al. | |
| 2013/0280573 A1* | 10/2013 | Taga ................... | H01M 2/1022 429/100 |
| 2015/0211534 A1* | 7/2015 | Volmer ............... | F04D 25/0673 417/45 |
| 2015/0328763 A1* | 11/2015 | Ito ............................ | H02J 7/00 451/359 |
| 2015/0367497 A1* | 12/2015 | Ito ............................ | B25F 5/02 173/217 |

FOREIGN PATENT DOCUMENTS

| | | | | |
|---|---|---|---|---|
| CN | 302663406 S | 11/2013 | | |
| CN | 104258638 A | 7/2015 | | |
| EP | 0944122 A1 * | 9/1999 | .......... | H02M 2/1022 |
| EP | 0944122 A1 | 9/1999 | | |
| JP | S60-138553 U | 9/1985 | | |
| JP | S63-88749 A | 4/1988 | | |
| JP | H1-230355 A | 9/1989 | | |
| JP | H01-230355 A | 9/1989 | | |
| JP | H5-344042 A | 12/1993 | | |
| JP | H05-344042 A | 12/1993 | | |
| JP | H10-144274 A | 5/1998 | | |
| JP | 2000-243361 A | 9/2000 | | |
| JP | 2008-257872 A | 10/2008 | | |
| JP | 2008257872 A * | 10/2008 | .......... | A47L 9/2884 |
| JP | 2008276945 A * | 11/2008 | .......... | H01M 2/1022 |
| JP | 2008-546445 A | 12/2008 | | |
| WO | 2014119192 A1 | 8/2014 | | |
| WO | WO-2014119192 A1 * | 8/2014 | .......... | A47L 9/2884 |

OTHER PUBLICATIONS

Extended European Search Report regarding Application No. 15889668.8, dated Jun. 7, 2018, 8 pages.
IP Australia Examination Report No. 1 regarding Application No. 2015392115, dated May 27, 2019, 4 pages.
IP Australia Examination Report No. 2 regarding Application No. 2015392115, dated Sep. 10, 2019, 4 pages.
Japanese Patent Office Decision of Refusal regarding Application No. 2017-512736, dated Jul. 30, 2019, 6 pages.
Japan Patent Office, "Notice of Reasons for Refusal," Application No. JP2017-512736, dated Mar. 5, 2019, 6 pages.
European Patent Office Communication pursuant to Article 94(3) EPC regarding Application No. 15889668.8, dated May 31, 2019, 6 pages.
State Intellectual Proper Office of the P.R. China, International Search Report of International Application No. PCT/CN2015/088743 (dated Jan. 26, 2016).
European Patent Office Communication pursuant to Article 94(3) EPC dated Jul. 31, 2020, regarding application No. 15889668.8, 4 pages.
Notice of Reasons for Refusal regarding Japanese Application No. 2017-512736, dated Oct. 1, 2020, 12 pages.

* cited by examiner

LOCKABLE FITTING STRUCTURE FOR AN ELECTRIC AIR-PURIFYING RESPIRATOR OF AN AUTO-DARKENING WELDING HELMET

CROSS-REFERENCE TO RELATED APPLICATIONS

This patent application is the U.S. national phase of International Patent Application No. PCT/CN2015/088743, filed Sep. 1, 2015, which claims the benefit of Chinese Patent Application No. 201510194247.6, filed on Apr. 22, 2015, which are incorporated by reference in their entireties herein.

FIELD

The present application generally relates to a lockable fitting structure for a battery of an electric air-purifying respirator of a welding helmet, especially an auto-darkening welding helmet.

BACKGROUND

For safety sake, welding helmets, especially auto-darkening welding helmets have been widely used on welding site. An auto-darkening welding helmet is generally equipped with an auto-darkening filter. The auto-darkening filter can work mainly because it is provided with a liquid crystal panel. The liquid crystal panel is transparent in case of no welding-arc ignition. The liquid crystal panel is changed into an opaque state just before the welding-arc ignition begins, such that an operator's eyes are protected. The auto-darkening welding helmet is usually provided with an adjustable knob or button. Before wearing the welding helmet, the operator has to set operating parameters, such as SENSITIVITY, delay time, shade, and weld mode or the like, of the auto-darkening filter by the knob or button. Thereafter, the operator can wear the welding helmet to carry out a welding operation.

In order to ensure that a wearer can normally breathe as the wearer's face is completely sheltered by the welding helmet and/or the wearer carrying out the welding operation can be protected in a severe working environment, for example in a dusty environment, an electric air-purifying respirator is usually provided for the welding helmet, especially the auto-darkening welding helmet. This electric air-purifying respirator is connected to the welding helmet by a hose. Ambient air is purified by the respirator and then pumped into the helmet by an air pump of the respirator such that the wearer has clean air to breathe.

The air pump of the electric air-purifying respirator is powered by a rechargeable battery. The rechargeable battery is releasably placed in a battery holder of the electric air-purifying respirator. Conventionally, the rechargeable battery is connected to the battery holder at a small number of positions, which may lead the battery to unexpected disengagement from the holder during the welding operation. If this case unfortunately happens, the wearer cannot breathe or inhale harmful air to do harm to him/her. Further, the electric air-purifying respirator is usually put on the wearer's waist. Sometimes, due to operational requirements, it is required to detach the rechargeable battery and replace it with a new one when the wearer is wearing the respirator. Therefore, if the rechargeable battery can be designed such that it can be readily detached or re-installed on the welding site, the wearer's working efficiency will be greatly enhanced.

SUMMARY

With respect to the problems mentioned above, the present application proposes an improved lockable fitting structure which is used between a rechargeable battery and a battery holder of an electric air-purifying respirator of an auto-darkening welding helmet, such that the rechargeable battery can be locked more reliably and it is convenient for a user to assemble or disassemble the rechargeable battery.

According to one aspect of the present application, a lockable fitting structure used for an electric air-purifying respirator of an auto-darkening welding helmet is provided, the electric air-purifying respirator comprising a housing and a battery device, a battery holder being formed in the housing, and the battery device being able to be detachably installed in the battery holder by the lockable fitting structure, wherein the lockable fitting structure comprises at lease four pairs of sliding joint structures formed on the battery device and the battery holder respectively and a locking structure provided in the battery device, wherein the sliding joint structures of each pair can be engaged with or disengaged from each other by sliding them relative to each other, wherein the locking structure comprises a button and a tongue capable to be actuated by the button, wherein the tongue is movable along a direction substantially perpendicular to a sliding direction of the sliding joint structure, and wherein after the sliding joint structures have been moved relative to each other in place, the tongue contacts a stop side of the battery holder to lock the pairs of sliding joint structures.

Optionally, the battery device comprises a casing in which the sliding joint structures and the locking structure are provided.

Optionally, at least a sliding guide structure is provided between the battery device casing and the electric air-purifying respirator housing, and the sliding guide structure has a guiding direction substantially parallel to the sliding direction of the sliding joint structure.

Optionally, the sliding guide structure comprises a straight groove provided in the battery device casing and a straight rib provided in the electric air-purifying respirator housing, and the straight rib is movably received in the straight groove.

Optionally, the sliding joint structures comprise seven pairs, at least one of which comprise a groove provided in the battery device casing and a lug, which is provided in the electric air-purifying respirator housing and is insertable into the groove.

Optionally, at least one pair of the sliding joint structures comprise two L-shaped lugs.

Optionally, the locking structure further comprises a force applying component movably installed in the battery device casing and a spring capable to act between the tongue and the battery device casing, wherein the force applying component is enabled to act on both the button and the tongue such that a driving force can be transferred between the button and the tongue by defection of an angle of 90°, and wherein the spring provides a biasing force for the tongue, by which biasing force the tongue is able to protrude from the battery device casing.

Optionally, the force applying component is a pivotal component which can be pivoted, and the pivotal component has two parts which are perpendicular to each other and contact the button and the tongue respectively.

Optionally, the locking structure is located between two pairs of the sliding joint structures.

Optionally, the button can be actuated along a direction substantially parallel to the sliding direction of the sliding joint structure.

Optionally, after a user has worn the electric air-purifying respirator, the actuating direction of the button is substantially perpendicular to the user's body direction.

Optionally, the stop side is substantially perpendicular to the sliding direction of the sliding joint structure.

According to another aspect of the present application, an electric air-purifying respirator for an auto-darkening welding helmet is provided, wherein the electric air-purifying respirator is equipped with the above-mentioned lockable fitting structure.

Due to the technical means of the present application, the battery device can be more firmly locked to the battery holder to avoid any unexpected disengagement therefrom. Moreover, when a user wearing the electric air-purifying respirator manually disassembles the battery device, it is convenient for him/her to observe the disassembling process and thus the working efficiency of the on-site user can be enhanced on site.

BRIEF DESCRIPTION OF THE DRAWINGS

The forgoing and other aspects of the present application will be well understood by the following description in combination with the drawings. It should be noted that although those drawings may be given in different proportions, they cannot be deemed affecting understanding to the present application. In the drawings.

DETAILED DESCRIPTION

Figure 1A:
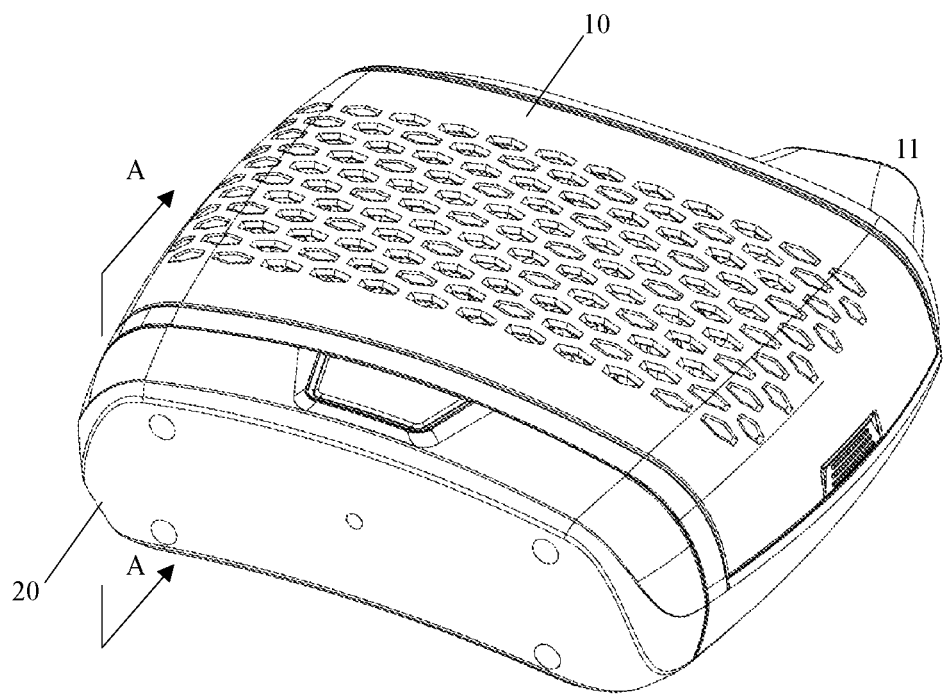
FIGS. 1a and 1b are a perspective view and a lateral view respectively, which schematically illustrate an electric air-purifying respirator according to an embodiment of the present application.

In the drawings of the present application, features having the same configuration or similar functions are represented by the same reference numerals.

Figure 1B:
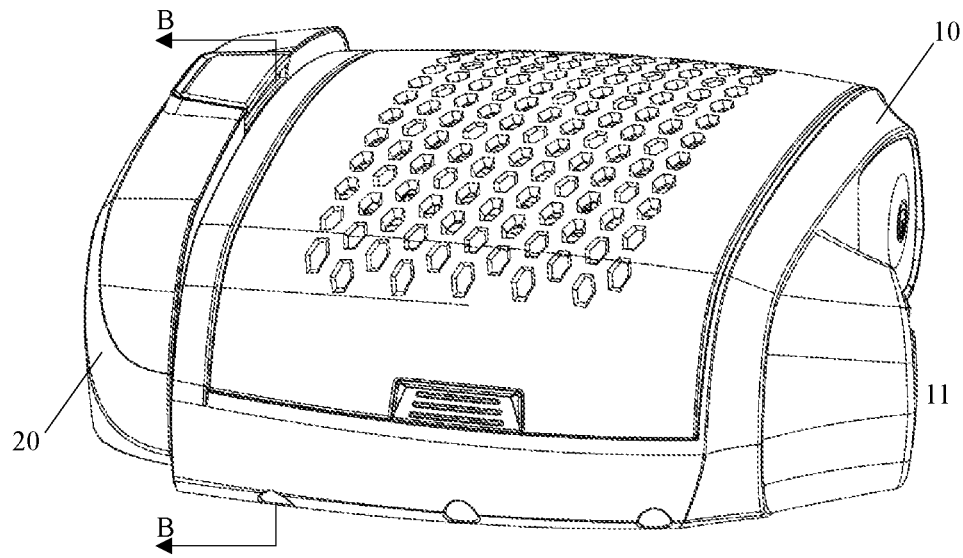

FIGS. 1a and 1b illustrate an electric air-purifying respirator according to one embodiment of the present application. The electric air-purifying respirator comprises a housing 10 and a battery device. The battery device comprises a casing 20 which is used detachably connect the housing 10. Components (not shown), such as an electric pump, an air-purifying device and a relevant control circuit or the like, are installed in the interior of the housing 10. A battery module (not shown) is installed in the interior of the casing 20 and is used to supply electric power for the electric pump.

A connecting port 11 is formed on an end side of the housing 10, and is used to be in communication with the air-purifying device in the housing 10. This connecting port 11 can be connected to a welding helmet, especially an auto-darkening welding helmet, by a connecting hose (not shown) such that purified air can be supplied to the helmet under the action of the electric pump. Both the housing 10 and the casing 20 are made of plastic.

A battery holder is formed on an opposite end side of the housing 10 and is used to receive the battery device casing 20. According to the present application, a lockable fitting structure is provided between the battery holder and the battery device casing 20, by which lockable fitting structure the battery device can be readily and firmly assembled onto the housing 10 of the electric air-purifying device. Furthermore, it is convenient for a wearer, who wears the welding helmet on his/her head, to disassemble the battery device.

Figure 2:
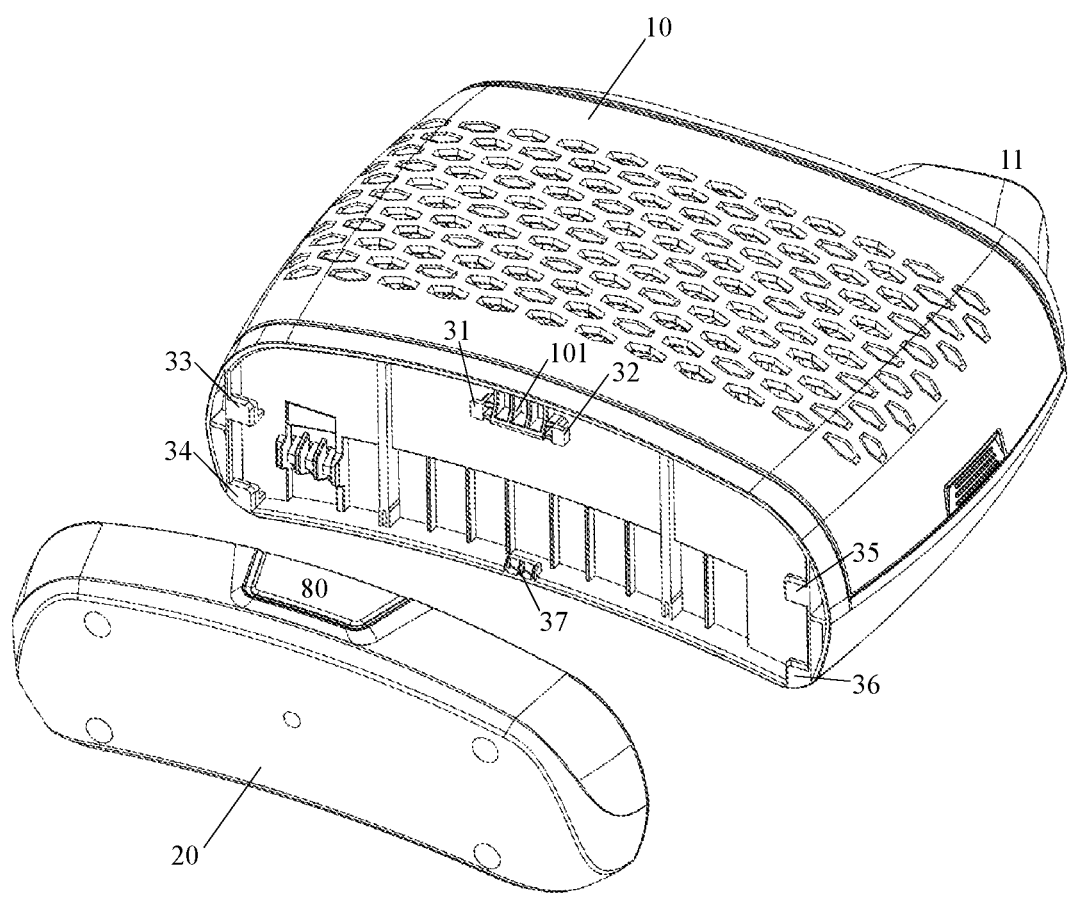
FIG. 2 is a perspective and exploded view, which schematically illustrates that a battery device of the electric air-purifying respirator has been disassembled from a battery holder.
Figure 3:
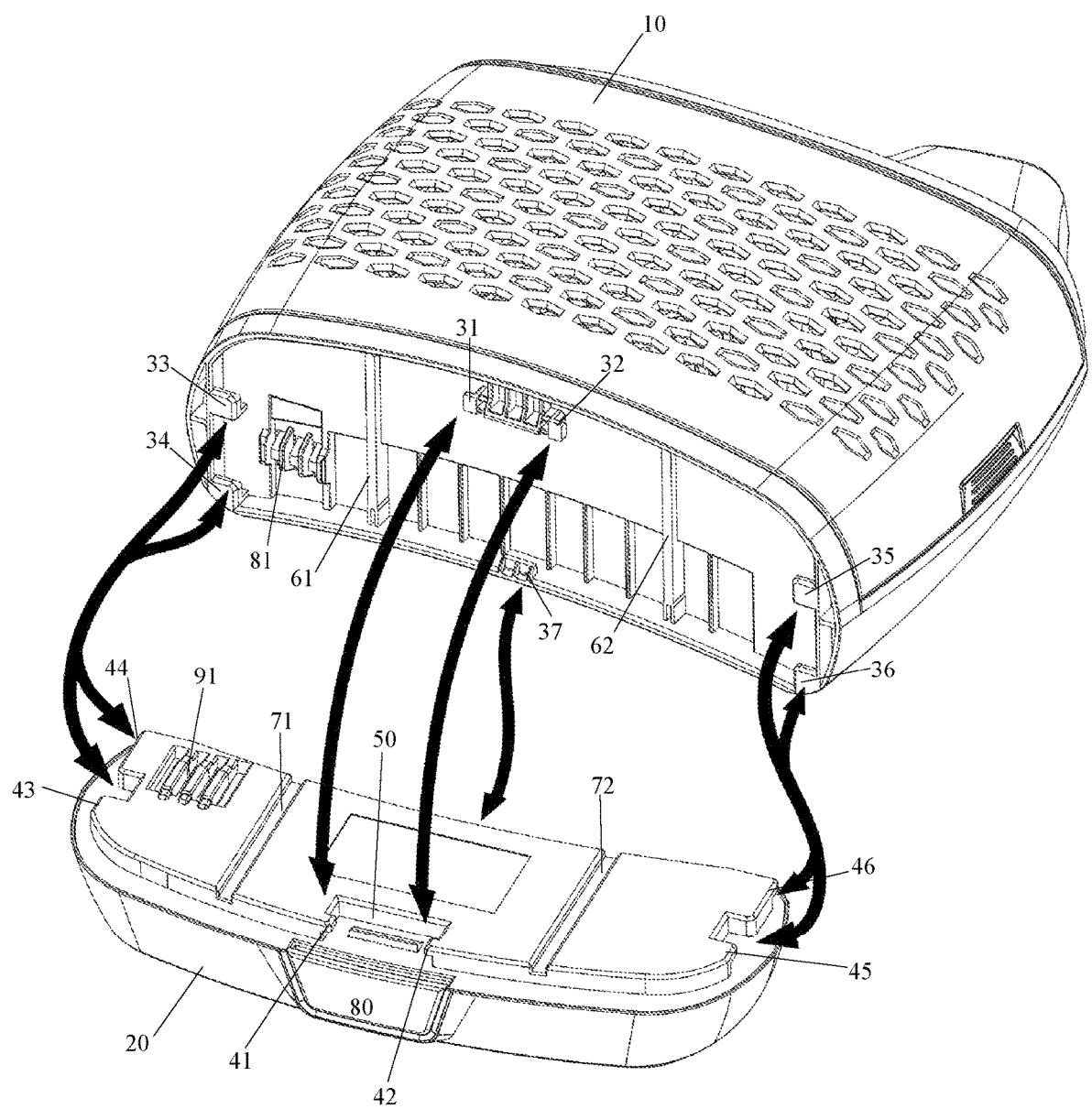
FIG. 3 schematically illustrates a lockable fitting structure between the battery device and the battery holder according to the present application.

FIG. 2 schematically illustrates that the battery device has been separated from the battery holder. FIG. 3 schematically illustrates engaging points of the lockable fitting structure between the battery device and the battery holder. Moreover, FIG. 3 also illustrates a side of the battery device casing 20 which can be fitted onto the battery holder.

Specifically, as shown in FIG. 3, the lockable fitting structure between the battery device casing 20 and the housing 10, especially the battery holder, of the electric air-purifying respirator is provided with seven engaging points such that latching between them can be achieved, as indicated by 7 double sided arrows in the view.

A pair of lugs 31 and 32 are formed on the housing 10 such that the lugs point in opposite directions. The pair of lugs can be placed into a receptacle 50 formed in the battery device casing 20. A pair of lugs 41 and 42, which oppose each other, are formed on two opposite sidewalls of the receptacle 50. The receptacle 50 is designed such that when it is required to fit the casing 20 onto the housing 10, the pair of lugs 31 and 322 are first received in the receptacle 50 at a position where they are slightly offset from the pair of lugs 41 and 42; and then, the lugs 41 and 42 in the receptacle 50 can be slid towards the lugs 31 and 32. Therefore, after being slid in place, the lugs 41 and 42 can contact the lugs 31 and 32 to prevent the casing 20 from further moving outwards relative to the housing 10.

Figure 4A:
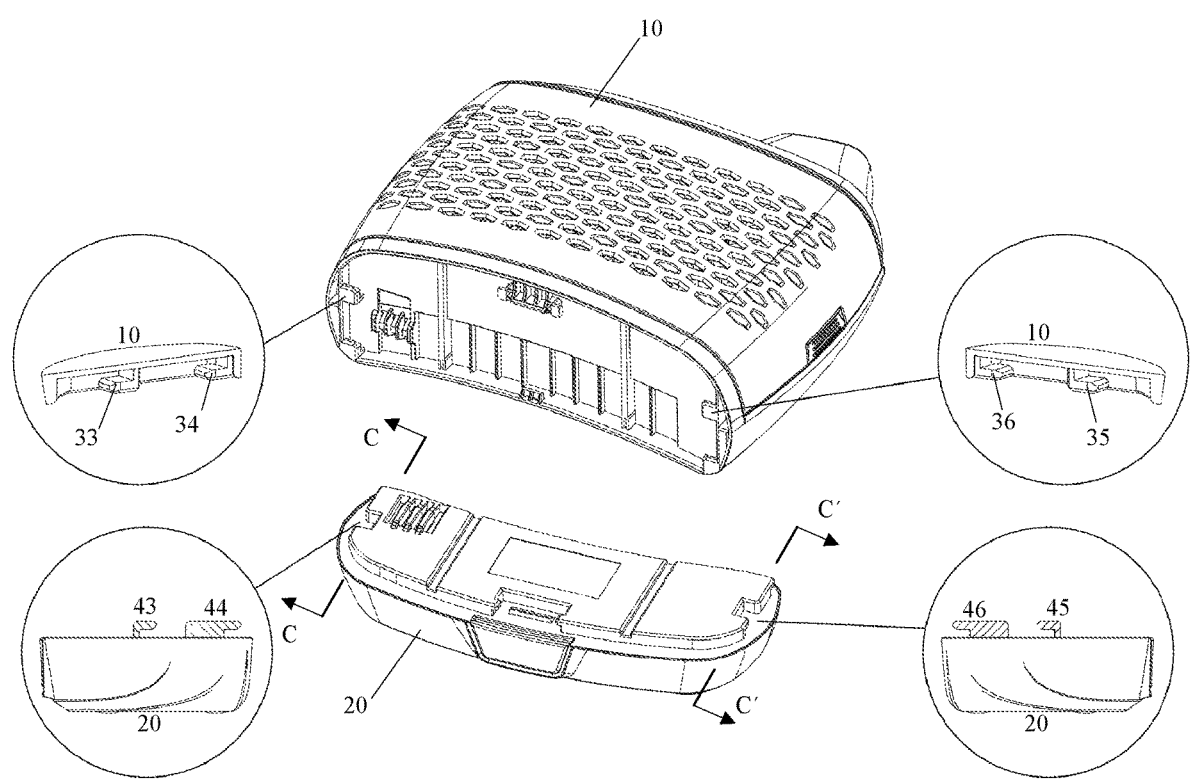
FIG. 4a schematically illustrates a part of the lockable fitting structure between the battery device and the battery holder, wherein circles represent enlarged perspective views and cross-sectional views respectively.

As shown in FIG. 4a, especially as shown by two upper circular portions in FIG. 4a, a pair of lugs 33 and 34 and a pair of lugs 35 and 36 are formed on the left and right sides of the pair of lugs 31 and 32 respectively. As shown by two lower circular portions (which are partial cross-sectional views obtained along arrows C-C and C'-C' of the casing 20), a pair of lugs 43 and 44 and a pair of lugs 45 and 46 are also formed on the battery device casing 20 at positions corresponding to those lugs 33 to 36. Viewed from the cross-sectional direction, those lugs 33, 34, 35, 36, and 43, 44 45, 46 are substantially L-shaped. Further, the L-shaped lugs on either the casing or the housing are bent in the same direction.

Figure 4B:
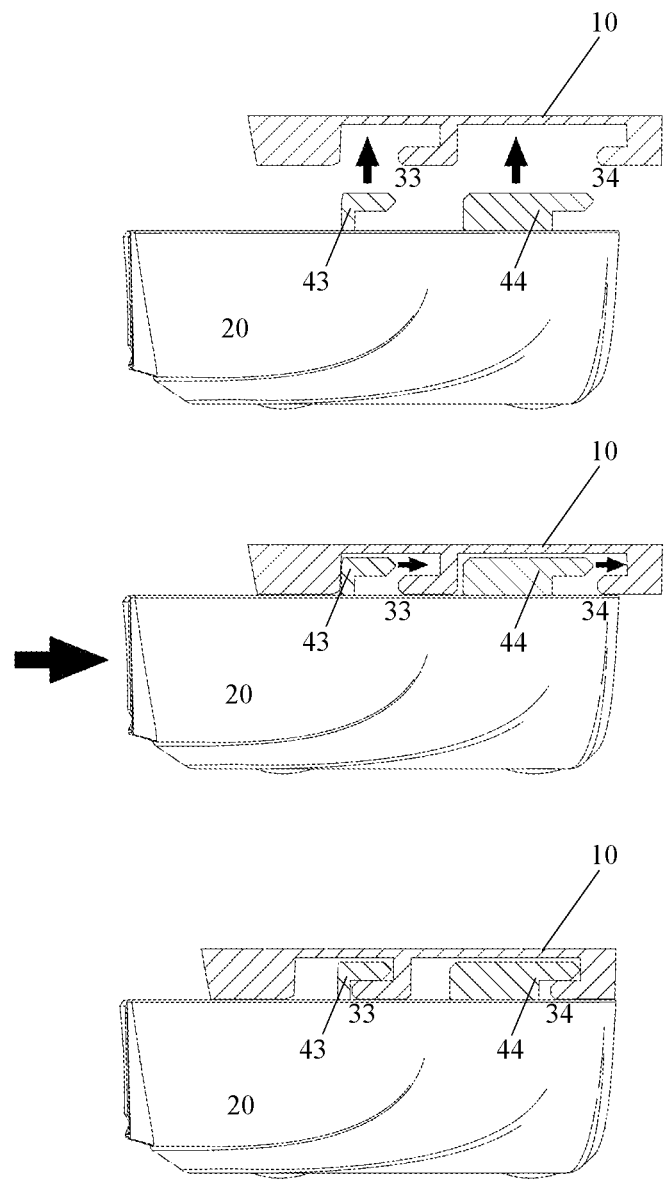
FIG. 4b is a cross-sectional view, which schematically illustrates how the battery device is slid and fitted onto the battery holder.

In order to illustrate how the battery device casing 20 is fitted onto the housing 10, further as shown in FIG. 4b, take the pair of L-shaped lugs 33 and 34 and the pair of L-shaped lugs 43 and 44 which are used to mate with them for example. FIG. 4b is a partially enlarged cross-sectional view obtained along an arrow A-A of FIG. 1a. Each of the lugs 33, 34, 43 and 44 defines a receiving pocket. Each receiving pocket has an opening. The openings are sized such that one lug can be received into the receiving pocket of anther associated lug in a direction along which the two lugs move close to or away from each other. For instance, as shown in FIG. 4b, when it is required to fit the battery device casing 20 onto the housing 10, the casing 20 is first moved towards the housing 10, as illustrated by the arrows, such that the lugs 43 and 44 enter the receiving pockets defined by the lugs 33 and 34 respectively (or in other words the lugs 33 and 34 enter the receiving pockets defined by the lugs 43 and 44); and then, the casing 20 contacts the housing 10 such that the L-shaped lugs 33 and 34 are offset from the L-shaped lugs 43 and 44 respectively; and then, the casing 20 is pushed relative to the housing 10 such that the casing can be slid relative to the housing and thus the lugs 33 and 34 contacts the L-shaped cantilevers of the lugs 43 and 44 respectively to prevent the casing 20 from further moving outwards relative to the housing 10.

A lug 37 is formed on the casing 20, which lug is located between the lugs 33, 34 and the lugs 35, 36 and substantially opposite to the lugs 31, 32. When the battery device casing 20 is slid onto the housing 10, the lug 37 can be received in a groove 47 (not shown in FIG. 2 but shown in FIGS. 6c and 6d only) of the casing 20. In this way, after the casing 20 is slid along one direction relative to the housing 10 in place, the lugs 31 and 41, the lugs 32 and 42, the lugs 33 and 43, the lugs 34 and 44, the lugs 35 and 45, the lugs 36 and 46, and the lug 37 and the groove 47 between the housing 10 and the casing 20 form said seven engaging points of the lockable fitting structure respectively, which are thus also called as sliding joint structures.

In order to ensure that the respective lugs can be aligned with each other or the respective lug and groove can be aligned with each other as the casing 20 is being slid on the housing 10, two straight grooves 71 and 72 are formed in the casing 20 such that the two straight grooves are substantially parallel to each other, and two straight ribs 61 and 62 are also formed in the housing 10 such that the two ribs are parallel to each other and at two positions corresponding to the straight grooves. In this way, when the casing 20 is attached over the housing 10, the straight ribs 61 and 62 are exactly received and guided by the straight grooves 71 and 72, respectively. The straight rib is matable with the straight groove to form a sliding guide structure.

Further, as shown in FIG. 3, a terminal 81 is formed on the housing 10 and a matable terminal 91 is formed on the casing 20 such that the terminal 81 is connected to the electric pump and the relevant control circuit in the housing 10 and the terminal 91 is connected to the battery module in the casing 20. Therefore, when the casing 20 is slid over the housing 10 in place, the terminal 81 engages the terminal 91 such that the battery module can supply electrical power for the electric pump and the relevant control circuit.

Figure 5:
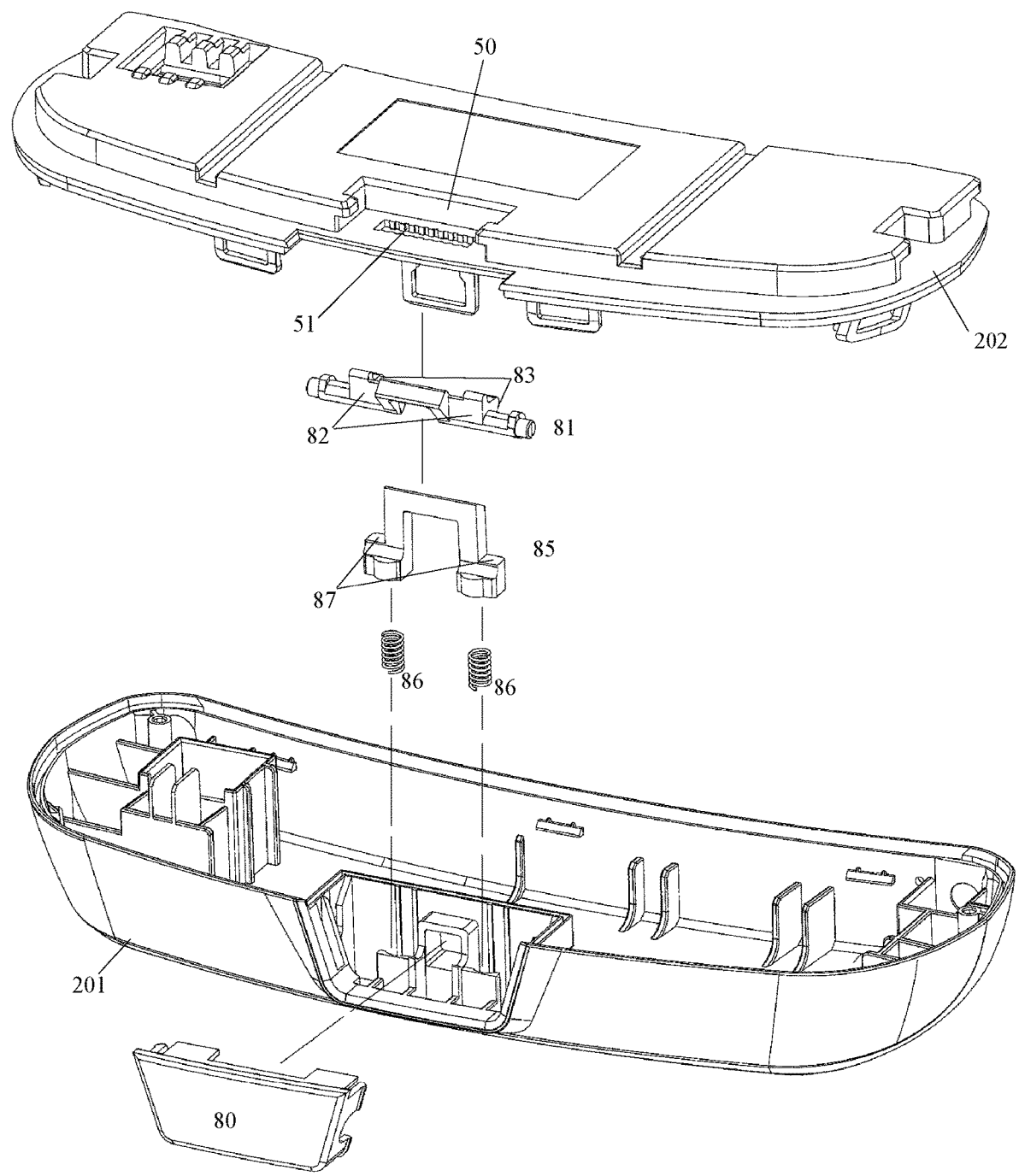
FIG. 5 is an exploded view, which schematically illustrates the battery device.

FIG. 5 is an exploded and perspective view further illustrating the battery device casing 20. As shown, the casing 20 comprises a base 201 and a cover 202, both of which can be detachably connected to each other in a suitable manner of snapping, screwing or the like such that a cavity can be defined between the base and the cover to receive the battery module and relevant electrical devices. When the battery device casing 20 is fitted onto the housing 10, the cover 202 faces and contacts the housing 10.

As shown in FIGS. 2 and 3 again, a protruding circumferential edge is formed on the end side of the housing 10.

All the lugs 31, 32, 33, 34, 35, 36 and 37 are integrally formed from the circumferential edge such that they are oriented radially and inwardly to form the battery holder by which the battery device casing 20 can be received. Further, the straight ribs 61 and 62 are also formed in an interior region enclosed by the circumferential edge.

As shown in FIG. 5, a boss is formed on an outwardly facing side of the cover 202. The lugs 41, 42, 43, 44, 45, 46, the receptacle 50 and the groove 47 are formed around the boss. Further, the boss has an area of projection which is less than an area of projection of the interior region enclosed by the circumferential edge of the battery holder such that the casing 20 can be slid to a certain extent after it is attached on the housing 10.

An opening 51 is provided on a bottom of the receptacle 50. A recess is formed in the base 201, in which recess a button 80 is installed such that it is linearly movable. A tongue 85 is supported in the recess such that it is linearly movable. The tongue 85 is movable in a direction substantially perpendicular to a moving direction of the button 80. A pivotal component 81 is pivotably installed in the recess, and a pair of springs 86 are also provided in the recess. One end of the spring 86 is securely received in the base 201 and the other end is securely received in the tongue 85, such that a spring force is constantly applied to the tongue 85 and thus enables the tongue to move outwardly relative to the base 201.

The pivotal component 81 is integrally formed with an active plane 82 and a protrusion part 83. The active plane 82 is substantially perpendicular to the protrusion part 83. In the embodiment illustrated by FIG. 5, the active plane 82 comprises two active planes and the protrusion part 83 comprises two protrusion parts. However, it can be conceived that the number of them can be set as required. For instance, only one active plane or protrusion part or a plurality of active planes or protrusion parts can be provided. A step face 87 is integrally formed on the tongue 85. This step face is used to contact the protrusion part 83 of the pivotal component 81, and one or more step faces can be provided. The number of the step faces can be set depending on the number of the protrusion parts. Therefore, in the embodiment illustrated by FIG. 5, the number of the step faces 87 is also two. A part of the button 80, for example a bump 88 (shown in FIG. 6a), can contact the active plane 82 of the pivotal component 81. Therefore, the pivotal component 81 can contact both the button 80 and the tongue 85. By actuating the button 80 to drive the pivotal component 81 to pivot about its pivotal axis by an angle, the tongue 85 can be moved to a certain extent.

Figure 6A:
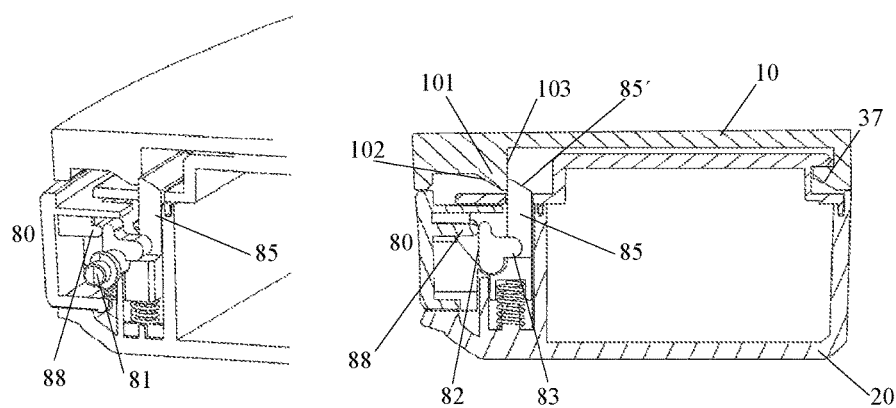
FIGS. 6a, 6b, 6c and 6d are enlarged detail views obtained along the arrows B-B of FIG. 1b, which respectively illustrate how the battery device is moved relative to the battery holder from a locked state to an unlocked state.
Figure 6B:
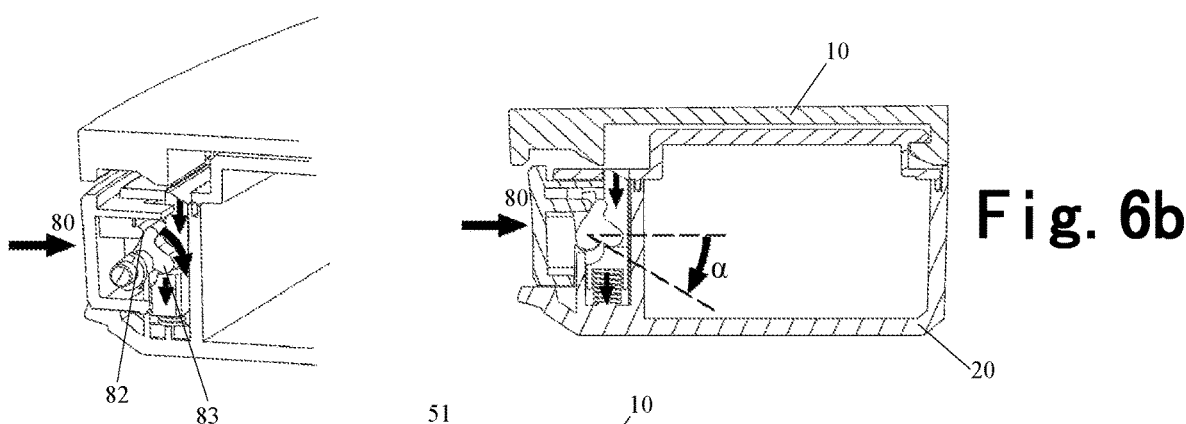
Figure 6C:
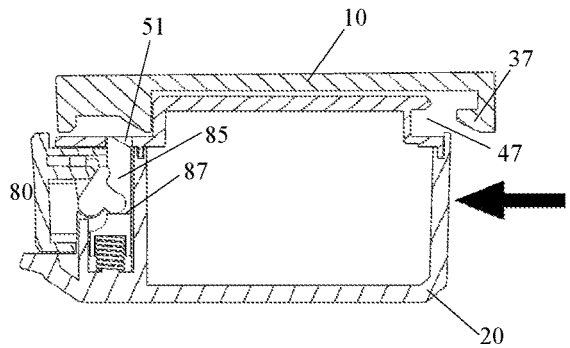
Figure 6D:
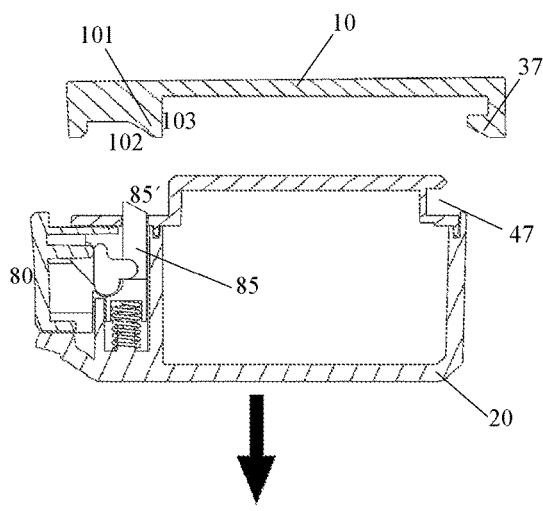

After the cover 202 has been assembled onto the base 201, an end of the tongue 85 can extend through the opening 51 and protrudes outwardly. As shown in FIG. 6a, a boss 101 is formed in the housing 10, especially in the battery holder. For example, this boss is located between the two lugs 31 and 32. This boss 101 has an oblique face 102 and a vertical stop side 103. The protruding end of the tongue 85 is formed with an oblique face 85'. As the casing 20 is being slid relative to the battery holder as shown in FIG. 4a, the oblique face 85' of the tongue 85 first contacts the oblique face 102 of the boss 101 such that the tongue 85 is pressed and thus its end is moved into the casing 20 through the opening 51. Afterwards, after the oblique face 102 moves over the end, the end is biased by the springs 86 to protrude from the opening 51 again. Therefore, the tongue 85 contacts the vertical stop side 103 of the boss 101 such that it is in a locked state, as shown in FIG. 6a, to avoid any unexpected disengagement of the lockable fitting structure between the housing 10 and the casing 20. It can be seen that the moving direction of the tongue 85 is substantially perpendicular to a sliding direction of the casing 20 or in other words the moving direction of the button 80 is consistent with the sliding direction of the casing 20. According to the present application, the tongue 85 can be locked in a direction substantially perpendicular to the direction along which the battery device casing 20 is slid relative to the battery holder, such that the casing 20 can be more reliably locked in place.

The oblique face 102 of the boss 101 and the oblique face 85' of the tongue 85 are designed such that the casing 20 can be slid into the battery holder more smoothly and, in the meanwhile, under the action of the springs 86, a "kappa" sound is made due to quick rebound of the oblique face 85' after the oblique face 102 is moved over it. In this way, a user is warned that the tongue 85 has been locked in place.

FIGS. 6a to 6d illustrate how to disassemble the battery device casing 20 from the housing 10. First, one's finger is used to press the button 80 inwardly such that the pivotal component 81 can be pivoted about its pivotal axis by an angle of a. Therefore, the end of the tongue 85 having the oblique face is retracted under the opening 51. Then, with the button 80 being pressed, the casing 20 is slid outwards relative to the battery holder by pulling or pushing it. Finally, the battery device casing 20 is removed.

As shown in FIGS. 1a, 1b and 2, a buckle is provided at either lateral side of the housing 10 and is used to fasten a belt. In use, the electric air-purifying respirator housing 10 can be secured on the user's abdomen or waist by the belt. In this way, the connecting port 11 is above the battery device and the button 80 is exposed outwardly such that it is convenient for the user to observe and operate them. When the user intends to replace or inspect the battery device, he/she can press the button 80 towards his/her body by one finger such that the old battery device can be detached and a new one can be installed again. In this whole process, the user can slightly lower his/her head to facilitate his/her eyes' observation and monitoring of the manual detaching operation.

It can be appreciated by a person skilled in the art that the positions of the straight grooves 71 and 72 and the straight ribs 61 and 62 can be exchanged. For example, in an alternative embodiment, two parallel straight ribs are formed in the casing 20, and two parallel straight grooves are formed in the housing 10 at positions corresponding to the straight ribs, respectively. Furthermore, the number of the straight grooves and ribs can be set as desired, for example as one or more.

In the illustrated embodiment, after the user has worn the electric air-purifying respirator, the casing 20 can be slid relative to the housing 10 along a direction substantially perpendicular to the ground, and parallel to his/her body's sagittal direction. As an alternative, it is feasible that by changing the orientation of the lugs, the lockable fitting structure can be designed such that the sliding direction of the casing is substantially parallel to the ground and the body's coronal direction.

Although in the illustrated embodiment the lockable fitting structure between the battery device and the battery holder of the electric air-purifying respirator housing has seven engaging points arranged around the battery holder, the number or arrangement manner of the engaging points can be modified as required. For example, as an alternative, one or more pairs of lugs can be cancelled from the lugs 31, 32, 33, 34, 35, 36 and the lugs 41, 42, 43, 44, 45, 46 or one or more pairs of lugs can be added into them to decrease or increase the number of the engaging points of the lockable fitting structure. As an alternative, the positions of the lug 37 and the groove 47 can be exchanged. For example, said lug can be provided in the casing 20 and said groove can be provided in the housing 10.

In the illustrated embodiment, the button 80, the pivotal component 86 and the tongue 85 constitute a locking structure. The button of said locking structure can be actuated along a direction substantially parallel to the sliding direction of the battery device relative to the battery holder. However, the tongue of said locking structure can be locked along a direction substantially perpendicular to the sliding direction of the battery device relative to the battery holder. This locking structure is located between the pair of the lugs 31 and 41 and the pair of the lugs 32 and 42. However, in an alternative embodiment, said locking structure can be provided at any position where operation can be facilitated. For example, it can be provided between the pair of the lugs 31 and 41 and the pair of the lugs 33 and 34.

Furthermore, in the illustrated embodiment, use of the pivotal component 81 enables the button 80 to be pressed and actuated along a direction substantially perpendicular to the moving direction of the tongue 85. However, it can be appreciated by the skilled person in the art that any other component for changing the direction of force can be used in the present application. For instance, the pivotal component 81 can be replaced with a translational wedge-shaped block. This wedge-shaped block has a vertical side for contacting the button 80 and an oblique side for contacting the tongue 85. Using said wedge-shaped block, an actuating force from the button 80 can be applied perpendicularly to the tongue 85 such that it can be driven to move correspondingly.

Using the lockable fitting structure of the present application between the battery device and the battery holder, the battery device can be firmly locked on the electric air-purifying respirator casing. Further, it is convenient for the user to manually disassemble the battery device.

Although some specific embodiments of the present application have been described here, they are given for illustrative purposes only and cannot be deemed limiting the scope of the present application in any manner. Various alternations, modifications and alternations can be conceived without departing from the spirit and scope of the present application.

The invention claimed is:

1. A lockable fitting structure used for an electric air-purifying respirator of an auto-darkening welding helmet, the electric air-purifying respirator comprising a housing and a battery device, a battery holder being formed in the housing, and the battery device being able to be detachably installed in the battery holder by the lockable fitting structure, wherein the lockable fitting structure comprises:
   at least four pairs of sliding joint structures formed on the battery device and the battery holder respectively; and
   a locking structure provided in the battery device,
   wherein the sliding joint structures of each pair can be engaged with or disengaged from each other by sliding them relative to each other,
   wherein the locking structure comprises:
      a button configured to be actuated in an actuating direction, and
      a tongue elastically biased in a direction substantially perpendicular to the actuating direction toward the electric air-purifying respirator housing and configured to be actuated by the button, wherein the tongue is movable along a direction substantially perpendicular to a sliding direction of the sliding joint structures, and wherein, after the pairs of sliding joint structures have been moved relative to each other in place, the tongue contacts a stop side of the battery holder to lock the pairs of sliding joint structures.

2. The lockable fitting structure as recited in claim 1, wherein the battery device comprises a casing in which the sliding joint structures and the locking structure are provided.

3. The lockable fitting structure as recited in claim 2, wherein:

at least one sliding guide structure is provided between the battery device casing and the electric air-purifying respirator housing, and the at least one sliding guide structure has a guiding direction substantially parallel to the sliding direction of the sliding joint structures.

4. The lockable fitting structure as recited in claim 3, wherein the sliding guide structure comprises:

a straight groove provided in the battery device casing; and a straight rib provided in the electric air-purifying respirator housing, wherein the straight rib is configured to be movably received in the straight groove.

5. The lockable fitting structure as recited in claim 2, wherein the sliding joint structures comprise seven pairs, at least one of which comprise a groove provided in the battery device casing and a lug, which is provided in the electric air-purifying respirator housing and is insertable into the groove.

6. The lockable fitting structure as recited in claim 1, wherein at least one pair of the sliding joint structures comprise two L-shaped lugs.

7. The lockable fitting structure as recited in claim 1, wherein the locking structure further comprises:

an eccentric arm movably installed in the battery device casing; and a spring capable to act between the tongue and the battery device casing, wherein the eccentric arm is configured to act on both the button and the tongue such that a driving force can be transferred between the button and the tongue by deflection of an angle of 90°, and wherein the spring provides a biasing force for the tongue, by which biasing force the tongue is able to protrude from the battery device casing.

8. The lockable fitting structure as recited in claim 7, wherein:

the eccentric arm is a pivotal component which can be pivoted, and the pivotal component has two parts which are perpendicular to each other and contact the button and the tongue, respectively.

9. The lockable fitting structure as recited in claim 1, wherein the locking structure is located between two pairs of the sliding joint structures.

10. The lockable fitting structure as recited in claim 1, wherein the button can be actuated along a direction substantially parallel to the sliding direction of the sliding joint structures.

11. The lockable fitting structure as recited in claim 1, wherein the stop side is substantially perpendicular to the sliding direction of the sliding joint structures.

12. An electric air-purifying respirator for an auto-darkening welding helmet, wherein the electric air-purifying respirator is equipped with a lockable fitting structure as recited in claim 1.

13. The electric air-purifying respirator as recited in claim 12, wherein, when the electric air-purifying respirator is worn by a user, the actuating direction of the button is substantially in a direction toward the user's body.

14. The electric air-purifying respirator as recited in claim 12, wherein the battery device comprises a casing in which the sliding joint structures and the locking structure are provided.

15. The electric air-purifying respirator as recited in claim 14, wherein:

at least one sliding guide structure is provided between the battery device casing and the electric air-purifying respirator housing, and the at least one sliding guide structure has a guiding direction substantially parallel to the sliding direction of the sliding joint structures.

16. The electric air-purifying respirator as recited in claim 15, wherein:

the sliding guide structure comprises a straight groove provided in the battery device casing and a straight rib provided in the electric air-purifying respirator housing, and the straight rib is movably received in the straight groove.

17. The electric air-purifying respirator as recited in claim 15, wherein the sliding joint structures comprise seven pairs, at least one of which comprise a groove provided in the battery device casing and a lug, which is provided in the electric air-purifying respirator housing and is insertable into the groove.

18. The electric air-purifying respirator as recited in claim 12, wherein at least one pair of the sliding joint structures comprise two L-shaped lugs.

19. The electric air-purifying respirator as recited in claim 12, wherein:

the locking structure further comprises a eccentric arm movably installed in the battery device casing and a spring capable to act between the tongue and the battery device casing, the eccentric arm is enabled to act on both the button and the tongue such that a driving force can be transferred between the button and the tongue by deflection of an angle of 90°, and the spring provides a biasing force for the tongue, by which biasing force the tongue is able to protrude from the battery device casing.

20. The electric air-purifying respirator as recited in claim 19, wherein:

the eccentric arm is a pivotal component which can be pivoted, and the pivotal component has two parts which are perpendicular to each other and contact the button and the tongue, respectively.

* * * * *